US009721781B2

United States Patent
Sedlacek et al.

(10) Patent No.: US 9,721,781 B2
(45) Date of Patent: Aug. 1, 2017

(54) DEVICE FOR MASS SPECTROMETRY

(71) Applicant: TESCAN Brno, s.r.o., Brno (CZ)

(72) Inventors: Libor Sedlacek, Brno (CZ); Jaroslav Jiruse, Blansko (CZ)

(73) Assignee: TESCAN Brno, s.r.o., Brno (CZ)

( * ) Notice: Subject to any disclaimer, the term of this patent is extended or adjusted under 35 U.S.C. 154(b) by 0 days.

(21) Appl. No.: 15/218,732

(22) Filed: Jul. 25, 2016

(65) Prior Publication Data

US 2017/0025264 A1 Jan. 26, 2017

(30) Foreign Application Priority Data

Jul. 24, 2015 (CS) ...................................... 2015-517

(51) Int. Cl.
*H01J 49/40* (2006.01)
*H01J 49/14* (2006.01)
*H01J 49/04* (2006.01)
*G01N 23/225* (2006.01)
*H01J 37/26* (2006.01)

(52) U.S. Cl.
CPC ........ *H01J 49/401* (2013.01); *G01N 23/2258* (2013.01); *H01J 49/142* (2013.01); *H01J 37/26* (2013.01)

(58) Field of Classification Search
USPC .... 250/281, 282, 286–288, 306, 307, 396 R, 250/399, 423 R, 424, 425, 492.1, 492.21, 250/492.3, 526; 315/111.81
See application file for complete search history.

(56) References Cited

U.S. PATENT DOCUMENTS

| | | | | |
|---|---|---|---|---|
| 3,930,155 A | * | 12/1975 | Kanomata ............. | H01J 37/252 250/288 |
| 5,714,757 A | * | 2/1998 | Itabashi ............. | G01N 23/2255 250/305 |
| 5,825,035 A | * | 10/1998 | Mizumura ........... | H01J 37/3056 250/423 R |
| 7,446,309 B2 | * | 11/2008 | Murayama .......... | H01J 49/0004 250/281 |

(Continued)

OTHER PUBLICATIONS

Akiya, Karen et al., TOF-SIMS analysis of lithium air battery discharge products utilizing gas cluster ion beam sputtering for surface stabilization, Surface and Interface Analysis, Apr. 2, 2014, Wiley Online Library.

(Continued)

*Primary Examiner* — Bernard Souw
(74) *Attorney, Agent, or Firm* — Thedford I. Hitaffer; Hitaffer & Hitaffer, PLLC

(57) ABSTRACT

A device for mass spectrometry in continuous operation can be equipped with a focused electron beam source or laser radiation source. It can further include a vacuum chamber, a stage for placing the specimen, and an ion beam column with a plasma source for producing a primary ion beam and a secondary ion mass spectrometer for secondary ion analysis. The ion beam column is connected to an inert gas source and to a reactive gas source and is modified for simultaneous introduction of at least two gases from the inert gas source and reactive gas source. The secondary ion mass spectrometer is of an orthogonal Time-of-Flight type to ensure the function with the ion beam column in continuous operation.

9 Claims, 1 Drawing Sheet

(56) References Cited

U.S. PATENT DOCUMENTS

| | | | | |
|---|---|---|---|---|
| 7,459,693 B2 * | 12/2008 | Park | ............... | H01J 49/066 250/281 |
| 7,851,749 B2 * | 12/2010 | Komatsu | ............... | H01J 49/142 250/287 |
| 7,956,321 B2 * | 6/2011 | Murayama | ............... | H01J 49/0004 250/281 |
| 8,747,624 B2 * | 6/2014 | Medoff | ............... | C10G 3/00 204/157.15 |
| 8,771,480 B2 * | 7/2014 | Medoff | ............... | C10G 3/00 204/157.15 |
| 2009/0085211 A1 | 4/2009 | Robison et al. | | |
| 2010/0193701 A1 | 8/2010 | Tabat et al. | | |
| 2010/0227308 A1 * | 9/2010 | Hashimoto | ............... | G01N 33/6848 435/4 |
| 2014/0329274 A1 * | 11/2014 | Bowen | ............... | G01N 33/6848 435/34 |
| 2015/0115148 A1 * | 4/2015 | Aoki | ............... | H01J 49/0004 250/282 |
| 2015/0115149 A1 * | 4/2015 | Aoki | ............... | H01J 49/0004 250/282 |

OTHER PUBLICATIONS

Industrial Property Office of the Czech Republic, Search Report for related foreign priority document CZ Application No. PV 2015-517, Mar. 14, 2016, Prague, Czech Republic.

\* cited by examiner

DEVICE FOR MASS SPECTROMETRY

CROSS-REFERENCE TO RELATED APPLICATIONS

This application claims priority from CZ Patent Application No. PV 2015-517, filed Jul. 24, 2015, the disclosure of which is incorporated herein by reference.

BACKGROUND OF THE INVENTION

Field of the Invention

The invention relates to a device for mass spectrometry in continuous operation, utilizing an ion beam column with a plasma source, which can also be further equipped with a focused electron beam source or a laser radiation source.

Electron microscopy is a well-known and frequently used technique for high-resolution imaging. It comprises a whole family of devices, such as the Scanning Electron Microscope (SEM), Transmission Electron Microscope (TEM) or Scanning Transmission Electron Microscope (STEM). Electron microscope typically consists of an electron beam source, a beam limiting apertures, beam forming optics, a vacuum chamber and a stage with a specimen holder that is usually motorized and provides movement in several different axes.

Electron microscopes are often additionally combined with the Focused Ion Beam (FIB) tool or Gas Injection System (GIS). The ion beam column typically consists of the ion source, beam limiting apertures and beam forming optics. Ion beam column are mainly classified by the type of the ion source. Most frequently used ion sources in electron microscopy are Liquid Metal Ion Source (LMIS), Gas Field Ion Source (GFIS) or plasma ion sources that can be of e.g., Electron Cyclotron Resonance (ECR) or Inductively Couple Plasma (ICP) type.

A general trend is to integrate also a large number of analytical devices into the electron microscope, such as characteristic x-ray radiation detectors like the Energy Dispersive X-ray Spectrometer (EDS) or Wavelength Dispersive X-ray Spectrometer (WDS), Electron Backscatter Diffraction (EBSD), Electron Beam Induced Current (EBIC) detector, Cathode Luminescence (CL) detector, Confocal Raman Microscope (CRM), Scanning Probe Microscope (SPM) like Atomic Force Microscope (AFM), Electron Energy Loss Spectrometer (EELS) and other.

Main benefit that comes from combining multiple devices into one vacuum analytical chamber is the in-situ imaging, machining, analysis and characterization of specimens. Moreover, individual devices benefit from each other. For example, SEM can be used not only for imaging, but it also serves as the primary beam for other techniques and it is useful to navigate over the specimen or to compensate for charging.

To ensure successful integration of individual tools into one device, it is necessary to adapt them accordingly. The aim is usually to get many different tools in one analytical chamber and to get all their pole-pieces the closest to one monitored specimen. This often concerns making them smaller or reducing the size of their pole piece, while maintaining their full functionality and the best parameters.

Efforts have been made to integrate also the Secondary Ion Mass Spectrometer (SIMS) with the electron microscope. It provides information on elemental or isotopic composition of the specimen and it is also capable of quantitative analysis. Such a specific combination is highly desired in electron microscopy.

SIMS is based on the detection of secondary ions that are created by sputtering the material from the specimen with a primary ion beam, the source of which is often FIB. The secondary ions are subsequently focused and transferred into the mass analyzer using the Ion Transfer Optics (ITO). Before reaching the detector, they are separated in the mass analyzer based on the ratio of their mass to the electrical charge in the electric field or magnetic field or time. There are several types of SIMS that differ mainly by the separation method of secondary ions. Sector Field Mass Spectrometers employ static electric and/or magnetic sector to separate ions in space, Quadrupole Mass Spectrometers (QMS) use one or more quadrupoles for that and Time-of-Flight (ToF) spectrometers are based on secondary ion separation in time.

Spectrometers employing ion separation in space can typically measure only a very limited portion of the mass spectrum at the same time, whilst all other secondary ions left unexploited. On the other hand, spectrometers based on ion separation in time can simultaneously measure the whole mass spectrum or a very large portion of it, which is very beneficial. Unfortunately, most of them function in a pulse mode of the primary ion source. This means that the primary ion beam is always generated only in a very short time frame, which is followed by the analysis of the secondary ions in the spectrometer. However, pulsing with the primary beam is not preferable in combined devices because it limits the utility or significantly slows down the analysis or it cannot be well implemented when FIB is used as a source of primary ion beam. For example, if it is necessary to remove large amounts of material, it is desirable to generate a high-current primary ion beam continuously in order to save time.

A capability to simultaneously measure a wide spectrum of the secondary ions while the specimen is continuously irradiated with the primary ion beam is only guaranteed by so called orthogonal ToF SIMS. The orthogonal design includes a pulse device capable of applying a high voltage electrostatic pulse on the secondary ions. It accelerates them in a direction perpendicular to their previous flight path. The higher the mass to charge ratio of the secondary ion is, the slower speed it gains and the later it reaches the detector. The specific mass to charge ratio of the secondary ion can be derived from its speed that can be calculated from its known time of flight over the known distance between the pulse device and the detector.

Only a small fraction of the species sputtered from the specimen by primary ion beam is ionized. Yield of secondary ions is a crucial parameter that significantly affects the sensitivity of the method. To increase the secondary ion yield, spectrometry often utilizes introduction of reactive gas, such as, for example, oxygen, iodine, cesium vapors or chlorine. Reactive gas typically adsorbs at the surface of the specimen, from which it is sputtered by a primary ion beam together with the specimen material, with which it subsequently reacts and helps to form more of its ions. For example, it is known that by introducing oxygen, the secondary ion yield of certain elements can be increased by 1-3 orders of magnitude.

It is preferable to use a GIS device to locally introduce the gas directly close to the analysis point on the specimen. Alternatively, it is possible to fill the entire chamber of the analytical device with the gas. However, from the point of integrated devices, neither of these methods is preferable, because in order to maintain high vacuum it is possible to use only a relatively small concentration of the reactive gas, which may also undesirably chemically interact with other parts of the devices, such as, for example, parts of ion or electron beam column or any other add-ons. The use of these methods is not very preferable for TOF SIMS in continuous operation. The reason for this is because when the primary ion beam continuously irradiates the surface of the specimen, e.g., when processing or scanning the specimen, the reactive gas cannot adsorb on the surface of the specimen in an ample amount and therefore the secondary ion yield is not sufficiently increased.

SUMMARY OF THE INVENTION

The object of the invention is a device for mass spectrometry consisting of a vacuum chamber, stage with a specimen holder, ion beam column with a plasma source and a Secondary Ion Mass Spectrometer for analyzing the secondary ions, wherein the ion beam column is connected to an inert gas source and a reactive gas source, and wherein the ion beam column is further adapted for a simultaneous introduction of at least two gasses from the inert gas source and the reactive gas source, and that the Secondary Ion Mass Spectrometer is an orthogonal Time-of-Flight type to ensure its function with the ion beam column in continuous operation.

In a preferable embodiment, the primary ion beam is focused. In another preferable embodiment, the plasma ion source of the ion beam column is of an ECR (Electron Cyclotron Resonance) type.

In another preferable embodiment, the reactive gas is oxygen.

In other preferable embodiments, the inert gas is xenon, argon or helium.

According to the preferable embodiment, the invention further includes a device for producing a focused electron beam, e.g., scanning electron microscope, or laser radiation source.

The object of the invention is utilizing the introduction of reactive gas directly into the plasma source, so that the primary ion beam contains ions of both, the inert gas and the reactive gas, and a ToF SIMS in orthogonal construction is used for mass spectrometry, employing the high voltage pulse for directing secondary ions and measuring their Time-of-Flight. Thus the ion beam column can work continuously. This is preferable for basic operations with the primary ion beam, such as processing or monitoring the specimen, independent of whether the SIMS measurement is taking place or not. Another advantage is that a standard ion beam column can be used, that is typically used in multiple-beam devices, without the need of its redesign for inclusion of the pulsing device for SIMS. The pulse device is part of the TOF analyzer and does not limit the ion beam column structurally or functionally. This creates an entirely unique technology, enabling the connecting of SIMS into the system with a plasma source ion beam column, device for producing a focused electron beam and, for example, a source of laser radiation, meant primarily for other operations, such as, for example, processing the specimen, deposition of any material on the specimen, or monitoring the specimen. This type of SIMS has an essential advantage over the other SIMS (segment or quadrupole type) in that it is capable of continuous measuring along the entire ion mass spectrum.

DETAILED DESCRIPTION OF THE PREFERRED EMBODIMENT

Figure 1:
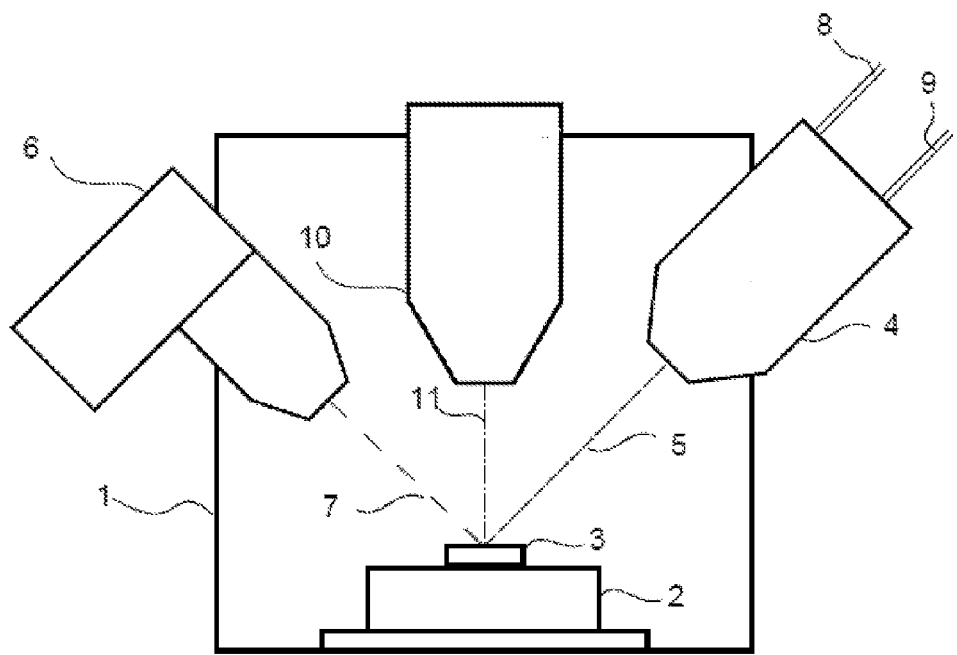
FIG. 1 schematically depicts an exemplary embodiment of a device with combined ion and electron beams and a Secondary Ion Mass Spectrometer according to the present invention.

An exemplary embodiment of the mass spectrometry device in continuous operation in FIG. 1 consists of the vacuum chamber 1 which contains the specimen stage 2 on which a studied specimen 3 is placed. The ion beam column 4 is then connected to the vacuum chamber, producing the primary ion beam 5, preferably focused, which serves to monitor the specimen 3, process the specimen 3 or to deposit any material onto the specimen 3. For many reasons, apparent to the person skilled in the art, it is preferable for monitoring or processing the primary ion beam 5 to be continuous, and at the same time monitor the material composition of the material sputtering from the area on the specimen 3. This is, for example, preferable in deducing which material is currently being sputtered from the specimen 3. This is provided by the orthogonal TOF-type SIMS 6 by analyzing secondary ions 7. An exemplary embodiment is provided by the compact version of the secondary ion mass spectrometer 6 with a smaller housing, which is particularly preferable in combined devices, which are provided not only with the ion beam column 4, but also, for example, the electron beam column 10 or a laser radiation source, these being the so-called multi-beam devices. The secondary ion 7 yield is dependent on the type of primary ions generated by the ion source, their quantity and energy, the angle of incidence of the focused primary ion beam, material composition of the specimen and other conditions. If the secondary ion 7 yield is small, the SIMS analysis cannot be done or it is not sensitive enough. An inert gas source 8, e.g., argon, xenon or helium and a reactive gas source 9, e.g., iodine, chlorine, oxygen or cesium vapors, are connected to the plasma source of the ion beam column 4 to gain a sufficient secondary ion yield. In a preferable embodiment, the ion beam column 4 is provided with an ECR type plasma source. In a preferred embodiment, xenon and oxygen are used to increase the positively charged ions yield, and a combination of xenon and cesium vapors is used to increase the negatively charged ions yield. Alternatively, it is possible to use other known types of plasma sources to produce primary ions.

The device for mass spectrometry in continuous operation can be preferably provided with an electron beam column 10 to form an electron beam 11. With its help, the specimen 3 can be displayed in higher resolution than the ion beam column 4 would allow. The most preferable is utilization of the scanning electron microscope 10. Alternatively, a transmission electron microscope 10 or scanning transmission electron microscope 10 can also be used. The device according to this description can be further provided with a source of laser radiation, for example, a femtosecond laser, which usually achieves higher processing speeds than the ion beam column 4 and is thus preferable to work higher volumes of the specimen.

Figure 2:
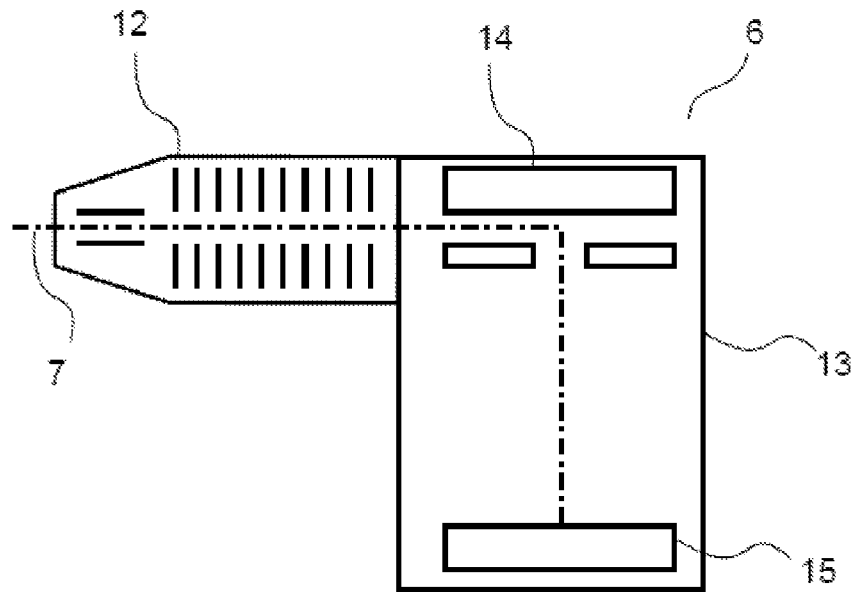
FIG. 2 schematically depicts a cross-sectional view of the orthogonal TOF SIMS.

The mentioned TOF SIMS 6 depicted in FIG. 2 is adapted for continuous measurement of a wide spectrum of ions. It utilizes a high-voltage pulse to accelerate the secondary ions 7, of which the time-of-flight is measured. First, the secondary ions 7 enter the secondary ion 7 transfer and focus optics 12, then the TOF SIMS chamber 13 and are accelerated by a high-voltage (HV) pulser 14, which in this embodiment is a high potential electrode. Secondary ions 7 with the same kinetic energy are directed over the known distances between the HV pulser 14 and the ion detector 15. Secondary ions 7 reach different speeds, based on the ratio of their mass to the charge. The secondary ion speed is determined from the known time of flight over a known distance, and a specific rate of mass to charge is added to it, from which the type of ion is determined. In one TOF SIMS 6 embodiment, secondary ions 7 are directed by the HV pulser 14 straight to an opposite detector, in another embodiment the ion detector 15 can be placed at an angle other than zero and secondary ions 7 can be directed to the ion detector 15 using an electrostatic mirror or similar particle optics elements. The ion detector can also, for example, be of the micro-channel plate multiplier type or other known types

LIST OF FIGURES

1—vacuum chamber
2—specimen stage
3—specimen
4—ion beam column
5—primary ion beam
6—secondary ion mass spectrometer
7—secondary ions
8—inert gas source
9—reactive gas source
10—electron beam column
11—electron beam
12—secondary ion transfer and focus optics
13—TOF SIMS chamber
14—HV pulser
15—ion detector

The invention claimed is:

1. Device for mass spectrometry including a vacuum chamber, stage for placing a specimen, ion beam column with a plasma source for producing primary ion beams and a secondary ion mass spectrometer for analyzing secondary ions, wherein the ion beam column is connected to an inert gas source and a reactive gas source, wherein the ion beam column is configured for continuously introduction of at least one gas from the inert gas source and at least one gas from the reactive gas source, and that the secondary ion mass spectrometer is of an orthogonal Time-Of-Flight type to ensure the function with the ion beam column in continuous operation.

2. Device for mass spectrometry according to claim 1, wherein the plasma source is of an Electron Cyclotrone Resonance type.

3. Device for mass spectrometry according to claim 1, wherein the ion beam column produces a focused ion beam.

4. Device for mass spectrometry according to claim 1, wherein the reactive gas source is an oxygen source.

5. Device for mass spectrometry according to claim 1, wherein the inert gas source is xenon source.

6. Device for mass spectrometry according to claim 1, wherein the inert gas source is argon source.

7. Device for mass spectrometry according to claim 1, wherein the inert gas source is helium source.

8. Device for mass spectrometry according to claim 1, further comprising a device for producing a focused electron beam.

9. Device for mass spectrometry according to claim 1, further comprising a laser radiation source.

* * * * *